United States Patent [19]
Hassett

[11] Patent Number: 5,814,029
[45] Date of Patent: Sep. 29, 1998

[54] GUIDING INTRODUCER SYSTEM FOR USE IN ABLATION AND MAPPING PROCEDURES IN THE LEFT VENTRICLE

[75] Inventor: James A. Hassett, Bloomington, Minn.

[73] Assignee: Daig Corporation, Minnetonka, Minn.

[21] Appl. No.: 661,094

[22] Filed: Jun. 10, 1996

Related U.S. Application Data

[63] Continuation-in-part of Ser. No. 388,800, Feb. 14, 1995, Pat. No. 5,640,944, Ser. No. 389,252, Feb. 16, 1995, Pat. No. 5,722,400, Ser. No. 333,791, Nov. 3, 1994, Pat. No. 5,564,440, and Ser. No. 333,759, Nov. 3, 1994, Pat. No. 5,628,316.

[51] Int. Cl.$^6$ ..................................................... A61M 25/00
[52] U.S. Cl. ........................... 604/281; 600/585; 606/41; 607/122
[58] Field of Search .................................. 600/374, 585; 606/41; 607/122; 604/280, 281

[56] References Cited

U.S. PATENT DOCUMENTS

| | | |
|---|---|---|
| 4,033,331 | 7/1977 | Guss et al. . |
| 4,117,836 | 10/1978 | Erirkson . |
| 4,581,017 | 4/1986 | Sahota . |
| 4,810,244 | 3/1989 | Allen . |
| 4,882,777 | 11/1989 | Narula . |
| 4,898,591 | 2/1990 | Jang et al. . |
| 4,935,017 | 6/1990 | Sylvanowicz . |
| 5,120,323 | 6/1992 | Shockey et al. . |
| 5,172,699 | 12/1992 | Svenson et al. . |
| 5,231,994 | 8/1993 | Harmjanz . |
| 5,242,441 | 9/1993 | Avitall . |
| 5,267,982 | 12/1993 | Sylvanowicz . |
| 5,279,546 | 1/1994 | Mische et al. . |
| 5,290,229 | 3/1994 | Paskar . |
| 5,304,131 | 4/1994 | Paskar . |
| 5,427,119 | 6/1995 | Swartz et al. . |
| 5,476,495 | 12/1995 | Kordis et al. . |
| 5,497,774 | 3/1996 | Swartz et al. . |
| 5,564,440 | 10/1996 | Swartz et al. ........................... 607/122 |
| 5,628,316 | 5/1997 | Swartz et al. ........................... 600/374 |
| 5,640,955 | 6/1997 | Ockuly et al. ........................... 600/374 |

*Primary Examiner*—Lee S. Cohen
*Attorney, Agent, or Firm*—Scott R. Cox

[57] ABSTRACT

A guiding introducer system for use in the treatment of arrhythmia associated with the left ventricle from the ventricular side comprising an inner guiding introducer and an outer guiding introducer wherein the inner guiding introducer is comprised of a first and second section and the outer guiding introducer is comprised of a first and second sections. The guiding introducer system is for use in sensing, pacing, and ablating procedures in the left ventricle.

9 Claims, 5 Drawing Sheets

GUIDING INTRODUCER SYSTEM FOR USE IN ABLATION AND MAPPING PROCEDURES IN THE LEFT VENTRICLE

This application is a continuation-in-part of application Ser. No. 08/388,800 filed on Feb. 14, 1995, now U.S. Pat. No. 5,640,944, application Ser. No. 08/389,252 filed on Feb. 16, 1995, now U.S. Pat. No. 5,722,400, application Ser. No. 08/333,791, filed Nov. 3, 1994, now U.S. Pat. No. 5,564,440 and application Ser. No. 08/333,759, filed Nov. 3, 1994 now U.S. Pat. No. 5,628,316.

BACKGROUND OF INVENTION

1. Field of Invention

This invention relates to sheaths or introducers. More particularly, this invention relates a guiding introducer system for mapping and ablation procedures in the left ventricle of the human heart.

2. Prior Art

Introducers and catheters have been in use for medical procedures for many years. For example, catheters have been used to convey an electrical stimulus to a selected location within the human body. Another use is monitoring and making measurements for diagnostic tests within the human body. Catheters are also used by physicians to examine, diagnose and treat while positioned at a specific location within the body which is otherwise inaccessible without more invasive procedures. In use, catheters are inserted into a major vein or artery which is near the body surface. These catheters are then guided to the specific location for examination, diagnosis or treatment by manipulating the catheter through the artery or vein of the human body.

Catheters have become increasingly useful in remote and difficult to reach locations within the body. However, the utilization of these catheters is frequently limited because of the need for the precise placement of the electrodes of the catheter at a specific location within the body.

Control of the movement of catheters to achieve such precise placement is difficult because of the inherent structure of a catheter. The body of a conventional catheter is long and tubular. To provide sufficient control of the movement of the catheter, it is necessary that its structure be somewhat rigid. However, the catheter must not be so rigid as to prevent the bending or curving necessary for movement through the vein, artery or other body part to arrive at the specified location. Further, the catheter must not be so rigid as to cause damage to the artery or vein while it is being moved within the body.

While it is important that the catheter not be so rigid as to cause injury, it is also important that there be sufficient rigidity in the catheter to accommodate torque control, i.e., the ability to transmit a twisting force along the length of the catheter. Sufficient torque control enables controlled maneuverability of the catheter by the application of a twisting force at the proximal end of the catheter that is transmitted along the catheter to its distal end. The need for greater torque control often conflicts with the need for reduced rigidity to prevent injury to the body vessel.

Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, generally with the aid of a guidewire and conventional introducer, through various arteries or veins until the tip of the catheter reaches the desired location in the heart.

The distal end of a catheter used in such a procedure is sometimes preformed into a desired curvature so that by torquing the catheter about its longitudinal axis, the catheter can be manipulated to the desired location within the heart or in the arteries or veins associated with the heart. For example, U.S. Pat. No. 4,882,777 discloses a catheter with a complex curvature at its distal end for use in a specific procedure in the right ventricle of a human heart. U.S. Pat. No. 5,231,994 discloses a guide catheter for guiding a balloon catheter for the dilation of coronary arteries. U.S. Pat. No. 4,117,836 discloses a catheter for the selective coronary angiography of the left coronary artery and U.S. Pat. Nos. 5,299,574 5,215,540, 5,016,640 and 4,883,058 disclose catheters for selective coronary angiography of the right coronary artery.

Conventionally, angiographic or balloon catheters are guided to the particular location within the heart, such as the coronary arteries, by use of a guidewire. During this procedure, the guidewire is first introduced into the vein or artery and is then advanced through the vasculature to the particular coronary artery to be analyzed. The catheter is then directed over the guidewire to the particular coronary artery. A conventional short straight introducer is often used to assist in introducing the coronary catheter into the vasculature, but is not used for advancing the coronary catheter through the vasculature to the coronary artery.

U.S. Pat. No. 5,242,441 discloses a deflectable catheter for ablation procedures in the ventricular chamber. See also U.S. Pat. No. 4,033,331. In addition, U.S. Pat. No. 4,898,591 discloses a catheter with inner and outer layers containing braided portions. The '591 patent also discloses a number of different curvatures for intravascular catheters.

Thus, catheters with predetermined shapes, designed for use during specific medical procedures generally associated with the heart or the vascular system have been disclosed.

In addition to single catheters with various curvatures, U.S. Pat. No. 4,581,017 discloses an inner and outer guide catheter, numbers 138 and 132, for use with a balloon catheter for treatment of coronary arteries. U.S. Pat. No. 5,120,323 discloses a guide catheter system for use in coronary arteries comprising an outer guide catheter (12) and a telescoping guide catheter (26), neither of which are precurved. U.S. Pat. No. 5,267,982 discloses a catheter assembly and methods for catheterization of coronary arteries wherein an inner catheter (50) and outer catheter (52) are used in combination for the treatment of right and left coronary angiographic procedures. See also U.S. Pat. No. 4,935,017 which discloses a similar device. U.S. Pat. No. 5,290,229 discloses a straight outer sheath and a preformed inner catheter for use in the heart. See also U.S. Pat. Nos. 5,304,131, 4,810,244 and 5,279,546.

U.S. Pat. No. 5,476,495 discloses a shaped guide sheath (166) for use in the right ventricle for ablation procedures.

Ablation procedures in the heart using a single, straight guide sheath have been disclosed. For example, catheter ablation of accessory pathways using a long vascular sheath by means of a transseptal or retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *J. Amer. Coll. Card.*, Vol. 21, no. 3, pps 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (February, 1993).

In addition, U.S. Pat. No. 5,427,119 discloses a shaped guiding introducer for introduction of an ablation and mapping catheter into the right atrium for the treatment of specific cardiac arrhythmia. U.S. Pat. No. 5,497,774 discloses the use of a guiding introducer for introduction of an ablation and mapping catheter into the left atrium for the treatment of specific cardiac arrhythmia.

U.S. Pat. No. 4,641,649 discloses the use of high frequency energy for the treatment of tachycardia or cardiac dysrhythmia. See also U.S. Pat. Nos. 5,246,438 and 4,945,912, which disclose the use of radio frequency energy for ablation of cardiac tissue. In addition, various articles have disclosed the ablation of specific locations within the heart by use of energy, in particular, radio frequency energy. See, for example, Gallagher, J. J. et al. "Catheter Technique for Closed-Chest Ablation of the Atrioventricular Conduction System" N. Engl. J. Med. Vol. 306, pp. 194–200 (1982); Horowitz, L. N. "Current Management of Arrhythmia" pp. 373–378 (1991); Falk, R. H. et al. "Atrial Fibrillation Mechanics and Management" pp. 359–374 (1992); and Singer, I. "Clinical Manual of Electrophysiology" pp. 421–431 (1993).

In addition, U.S. Pat. No. 5,172,699 discloses a general process for the identification and ablation of ventricular tachycardia sites. See also U.S. Pat. Nos. 5,222,501 and 5,242,441.

In addition, the use of radio frequency ablation energy for the treatment of Wolff-Parkinson-White Syndrome in the left atrium by use of a transseptal sheath is disclosed in Swartz, J. F. et al. "Radiofrequency Endocardial Catheter Ablation of Accessory Atrioventricular Pathway Atrial Insertion Sites" Circulation 87:487–499 (1993). See also Tracey, C. N. "Radio Frequency Catheter Ablation of Ectopic Atrial Tachycardia Using Paced Activation Sequence Mapping" J. Am. Coll. Cardiol. 21:910–917 (1993).

While a number of references have disclosed ablation procedures in the heart utilizing sheaths and catheters, there is still a need for new methods for the introduction of ablation catheters to specific locations in the heart, including specifically the left ventricle.

Accordingly, it is an object of this invention to disclose a guiding introducer system for selected medical procedures associated with the left ventricle of the human heart.

It is a further object of this invention to disclose a guiding introducer system for use in selected electrophysiology procedures associated with the left ventricle of the human heart.

Another object of this invention is to disclose a guiding introducer system for use in selected ablation procedures associated with the left ventricle of the heart.

It is a still further object of this invention to disclose a guiding introducer system for use in the selected ablation of sites associated with the mitral valve from the ventricular side for the treatment of left ventricular tachycardia.

These and other objects are obtained by the design of the guiding introducer system disclosed in the instant invention.

SUMMARY OF INVENTION

The instant invention is a guiding introducer system for use in the treatment of left ventricular tachycardia from the ventricular side. It may also be used to ablate locations under the mitral valve from the ventricular side, for example, for the treatment of Wolff-Parkinson-White syndrome ("WPW"). It is comprised of a precurved, inner guiding introducer and a precurved, outer guiding introducer. A precurved dilator is preferably used with the guiding introducer system, which dilator is preferably used with a Brockenbrough needle. The inner guiding introducer is comprised of a first and second section, wherein the first section is a generally elongated straight section which is merged at its distal end with the second section, which is a curved section. The outer guiding introducer is comprised of a first and second sections, wherein the first section is a generally elongated straight section which is merged at its distal end with the second section which forms a compound curved section. The inner guiding introducer is longer than the outer guiding introducer to permit it to extend out from the lumen of the outer guiding introducer to form various curves and shapes of the overall guiding introducer system.

DESCRIPTION OF THE INVENTION

A typical human heart includes a right ventricle, a right atrium, left ventricle and left atrium. The right atrium is in fluid communication with the superior vena cava and the inferior vena cava. The atrioventricular septum separates the atria from the ventricles. The tricuspid valve contained within the atrioventricular septum communicates the right atrium with the right ventricle. The mitral valve contained within the atrioventricular septum communicates the left atrium with the left ventricle. On the inner wall of the right atrium, where it is connected with the left atrium, is a recessed portion, the fossa ovalis. Between the fossa ovalis and the tricuspid valve is the opening or ostium for the coronary sinus. The coronary sinus is a large epicardial vein which accommodates most of the venous blood which drains from the myocardium into the right atrium.

In the normal heart, contraction and relaxation of the heart muscle (myocardium) takes place in an organized fashion as electrochemical signals pass sequentially through the myocardium from the atrial to the ventricular tissue along a well defined route which includes the His-Purkinje system. Initial electric impulses are generated at the sinoatrial (SA) node and conducted to the atrioventricular (AV) node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. For example, patients diagnosed with WPW have an arrhythmia, the cause of which is believed to be the existence of an anomalous conduction pathway or pathways that connect the atrial muscle tissue directly to the ventricular muscle tissue, thus by-passing the normal His-Purkinje system. These pathways are usually located in the fibrous tissue that connects the atrium and the ventricle.

Another arrhythmia is ventricular tachycardia ("V.T."). VT is a disease of the ventricles of the heart in which the heart's normal arrhythmic contraction is altered. Frequently, the rate of heart beat is too fast, although the conditions of the disease itself are generally quite complex. VT occurs most often in patients following a myocardial infarction. A myocardial infarction, commonly referred to as a heart attack, is a loss of blood to a region of the heart causing the myocardial tissue in that region to die and be replaced by an area of scar tissue known as a myocardial infarct. Frequently, the myocardial infarct is present in the left ventricle.

As a result of the myocardial infarct, circular pathways ("reentry circuits") are frequently created within the left ventricle which conduct electrical impulses of the heart. These reentry circuits cause the electrical impulses of the heart to travel in circles about the myocardial infarct, frequently causing an erratic and sometimes accelerated beating of the heart. These reentry circuits may also occur around discreet elements of the heart, such as valves. In addition, the reentry circuits sometime occur around both the myocardial infarct and the discreet elements of the heart.

In the past arrhythmia have been generally treated by the use of drugs, such as lidocaine, quinidine and procainamide. More recently, beta-blocking drugs have been used for this treatment. In cases where drug therapy has been ineffective, surgical procedures have sometimes been used to excise the tissue causing the arrhythmia. The procedure involves the removal of a portion of the heart muscle, particularly that portion around which the reentry circuit has formed. By the excision of this portion of the heart muscle, scar tissue is formed which prevents the reformation of the reentry circuit. Obviously such procedures are high risk, frequently requiring prolonged periods of hospitalization and recuperation. As an alternative to these procedures, ablation devices have been used for the diagnosis and treatment of cardiac arrhythmias. See, for example, U.S. Pat. No. 5,222,501. Also, guiding introducers have been used to guide ablation catheters for the treatment of atrial arrhythmias in U.S. Pat. Nos. 5,497,724 and 5,427,119.

Ablation procedures, however, are frequently unsuccessful unless repeated many times. It is presumed that one reason for the lack of success of ablation of ventricular tissue is the failure to destroy completely the reentry circuit in the ventricular tissue because of its inherent thickness and the size of the reentry circuit itself. To effectively ablate the ventricular tissue, the ablation catheter must be positioned precisely within the ventricle and maintained in contact with the ventricular tissue throughout the ablation procedure. Such procedures may require the ablation electrode of the ablation catheter to remain in contact with the ventricular tissue for a period of time well over a minute. This is particularly difficult when the heart is beating, sometimes irregularly, during the entire ablation procedure. Thus, it is critical that the ablation electrode be maintained at the desired location and also be constrained from movement throughout the ablation procedure.

Historically, there are two approaches to the positioning of an ablation catheter in the left ventricle for ablation procedures. The first approach is to introduce the catheter into the femoral artery using a standard introducer and advance it up the aorta, across the aortic valve into the left ventricle and then position its electrode adjacent to a wall of the left ventricle. This is commonly referred to as a "retrograde" approach. This approach is discussed in patent application Ser. No. 08/388,800 filed Feb. 14, 1995 and patent application Ser. No. 08/389,252 filed Feb. 16, 1995. Specific locations for the mapping or ablation of the ventricular tissue, include locations on the lateral freewall, posterior freewall, septal wall and anterior freewall. The retrograde approach to the left ventricle for ablation procedures is frequently difficult for many reasons including the structure of the left ventricle, the fact that it requires arterial access and potential problems associated with ablation of ventricle tissue, such as the creation of a substrate for a future arrhythmia which could result in sudden cardiac death. Thus, this retrograde approach is not preferred.

A second approach to positioning an ablation catheter for treatment of arrhythmia located in the left ventricle is from the atrial side of the mitral valve. This approach is referred to as the transseptal approach as the ablation catheter passes through the interatrial septum between the right and left atria. In this procedure, a transseptal sheath apparatus, comprising a conventional transseptal introducer, such as is produced by Daig Corporation, is introduced into the right femoral vein and advanced through the inferior vena cava into the right atrium. A puncture is then made through the interatrial septum, preferably at the fossa ovalis, and the apparatus is then advanced into the left atrium where the needle and dilator of the apparatus are removed leaving the introducer in place in the left atrium. An ablation catheter is then advanced through this introducer adjacent to or through the mitral valve for treatment of various arrhythmia associated with the left ventricle.

Mere introduction of the ablation and mapping catheter into the left ventricle is not sufficient to effectively and efficiently perform the ablation procedures to eliminate arrhythmia located in the left ventricle. The medical practitioner commonly monitors the introduction of the catheter and its progress through the vascular system by a fluoroscope. Such fluoroscopes can not easily identify the specific features of the heart in general, and the critically important structures associated with the left ventricle in specific, thus making placement of the ablation electrode difficult. This placement is especially difficult as the beating heart is in motion. As a result, the catheter is moving within the chambers of the heart as blood is being pumped through the heart throughout the procedure. The guiding introducer system of the instant invention addresses and solves these problems.

Referring now to FIGS. 1 through 4, the guiding introducer system of the present invention for procedures in the left ventricle for the treatment of arrhythmia associated with the mitral valve from the ventricular side, such as WPW, and various ventricle tachycardia is comprised of an inner and outer guiding introducer. See FIGS. 1A, 1B, 2A and 2B. Each introducer is divided into a first and second sections. (Each section is preferably formed as an integral portion of the entire guiding introducer without discrete divisions. However, the division of each guiding introducer into different sections better illustrates the overall shape of the guiding introducers.) Each of the guiding introducers will be shown in two views. See FIGS. 3A, 3B, 4A and 4B. In each of the views for ease of analysis, the guiding introducer will be secured to a hemostasis valve with side port for attachment to conventional side port tubing and a stop cock. In each such arrangement, the shape of the guiding introducer and each of its sections will be described, making reference to its position in relation to the side port which is attached to the proximal end of the guiding introducer.

The guiding introducer system for use in the left ventricle is comprised of an inner and an outer guiding introducer. See FIGS. 2A and 2B. A dilator is also preferably used, wherein the dilator preferably is a transseptal dilator used with cardiac procedures requiring a Brockenbrough needle for a transseptal puncture. Generally the distal end of the dilator is curved in a curve with an arc of about 20 to about 70 degrees ending in its distal tip. The overall length of the dilator is conventional.

The inner guiding introducer is generally comprised of two sections. See FIGS. 3A and 3B. The first section is a conventional generally elongated, hollow straight section of sufficient length for introduction into the patient and for manipulation from the point of insertion to the specific desired location within the heart. Merged with the distal end of the first section of the guiding introducer, but an integral part of the entire guiding introducer, is the second section which is a curved section, curved with a radius of about 0.5 to about 1.5 in., preferably from about 0.7 to about 1.3 in. and most preferably about 0.9 to about 1.1 in. to form an arc of approximately 45 to about 135 degrees, preferably about 60 to about 120 degrees, and most preferably about 70 to about 110 degrees ending in a distal tip.

The outer guiding introducer for use in the left ventricle is comprised of a first and second sections. See FIGS. 4A and 4B. The first section is a conventional, generally elongated hollow straight section of sufficient length for introduction into the patient and for manipulation from the point of insertion to the specific desired location within the heart. Merged with the distal end of the first section of the guiding introducer is the second section which is preferably a compound curved section curving first in a first curved portion with a radius of about 0.5 to about 1.5 in., preferably from about 1.0 to about 1.4 in., and most preferably about 1.1 to about 1.3 in. with an arc of approximately 10 to about 50 degrees, preferably about 10 to about 30 degrees and most preferably about 15 to about 25 degrees. Following the first curved portion is the second curved portion which curves with a radius of about 0.5 to about 1.5 in., preferably from about 0.7 to about 1.3 in., and most preferably about 0.9 to about 1.1 in. with an arc of approximately 135 to about 225 degrees, preferably from about 170 to about 210 degrees and most preferably about 180 to about 200 degrees ending in the distal tip of the outer guiding introducer. Preferably, the first and second curved portions are generally co-planar, preferably within about 20 degrees of being within the same plane. As an alternative to the compound curved section, a single curved portion may be used wherein the radius of this single curved portion is from about 0.5 to about 1.5 in., preferably from about 0.8 to about 1.2 in. and most preferably about 0.9 to about 1.1 in. with an arc from about 145 to about 260 degrees, preferably from about 180 to about 240 degrees and most preferably about 200 to about 220 degrees ending in the distal tip of the second section of the outer guiding introducer.

While the above described shapes are preferred, the shape of the sections of each guiding introducer of the guiding introducer system may be modified by use of one or more straight or curved sections as long as the overall, general shape of each of the guiding introducers is approximately as described above. In addition, the particular order of the curves may be changed as long as the overall curvature of each of the guiding introducers delivers the mapping and ablation catheter to approximately the same location as the guiding introducer system above described as the preferred embodiment. Further, one or more curves of the guiding introducers may be combined or split into additional curved or curved and straight sections as long as the general overall shape of the precurved, guiding introducers is maintained.

The design feature of the guiding introducer system provides a stable platform supported by the cardiac anatomy to permit an ablation or mapping catheter to be advanced and withdrawn without the need for repositioning the guiding introducer system. By extending the distal tip of the inner guiding introducer away from the distal tip of the outer guiding introducer and by rotating the inner guiding introducer with respect to the outer guiding introducer, a variety of shapes of the guiding introducer system are formed to direct the mapping and/or ablation catheter toward a particular site within the left ventricle. See FIGS. 1A and 1B where the distal end of the inner guiding introducer is rotated and/or extended to permit the ablation catheter contained therein to ablate various locations within the left ventricle. These shapes permit ablation procedures to be performed in the left ventricle associated with the mitral valve annulus from the ventricular side, for example, in a position anterior to anterolateral to lateral to posterolateral to posteroseptal to septal to the mitral valve. See FIG. 1B. In addition, by adjusting the extension and direction of the inner guiding introducer within the outer guiding introducer, ablation and mapping catheters can be directed for procedures on the left ventricular anterior free wall and toward the septal wall for treatment of Belhassen Tachycardia. See FIG. 1A. The various locations can be treated by extending the inner guiding introducer further from the outer guiding introducer which forms a different overall shape and/or by rotating the inner guiding introducer with respect to the outer guiding introducer. Being able to extend the inner guiding introducer within the outer guiding introducer and to rotate the inner guiding introducer within the outer guiding introducer permits a wide variety of overall shapes, which is particularly useful to medical practitioners. The medical practitioner is able to determine the relative location of the inner and outer guiding introducers because of tip markers located near the distal tip of both the inner and outer guiding introducers.

The distal tip of both the inner and outer guiding introducers may be, and generally will be, tapered to form a good transition with the dilator.

The relative size of the outer guiding introducer in relation to the inner guiding introducer should be sufficient to permit the inner guiding introducer to be torqued or rotated within the outer guiding introducer without undue restriction on such movement. Preferably, the difference in size between the inner and outer guiding introducer should be at least about 3 "French" (1 French equals about one-third of a millimeter). For example in one preferred embodiment, the outer guiding introducer is 11 French in size and the inner guiding introducer is 8 French. By this difference in diameter, there is approximately 1 French unit of volume available between the outer surface of the inner guiding introducer and the inner surface of the outer guiding introducer. Preferably, this volume of space between the inner and outer guiding introducer is filled with a biocompatible solution, such as a saline solution, preferably a heparinized saline solution. This saline solution also provides lubricity to the two guiding introducers, allowing more accurate torquing of the inner guiding introducer within the outer guiding introducer. In addition, it is preferable that the structure of both the inner and the outer guiding introducer have a high torsional constant to allow for the full utilization of the various shapes available by rotation and extension of the inner and outer guiding introducer. To permit this high torsional constant, in one preferred embodiment the inner guiding introducer is braided to provide further strength and structural stability.

The guiding introducers may be made of any material suitable for use in humans, which has a memory or permits distortion from and subsequent substantial return to the desired three dimensional shape. For the purpose of illustration and not limitation, the internal diameter of the tip of the guiding introducers may vary from about 6 to about 10 "French" Such guiding introducers can accept dilators from about 6 to about 10 French and appropriate guidewires. Obviously if larger, or smaller dilators and catheters are used in conjunction with the guiding introducers of the instant invention, modification can be made in the size of the instant guiding introducers.

The inner and outer guiding introducers also preferably contain one or a plurality of vents near the distal tip of the guiding introducers, preferably 3 or 4 of such vents. The vents are preferably located no more than about 5 to 6 cm. from the tip of the guiding introducers and more preferably 0.5 cm. to about 4.0 cm. from the tip. The size of these vents should be in the range of about 20 to 60 $\frac{1}{1000}$ of an inch in diameter. These vents are generally designed to prevent air embolisms from entering the guiding introducers caused by the withdrawal of a catheter contained within the guiding introducers in the event the distal tip of one of the guiding introducers is occluded. For example, if the tip of the inner guiding introducer is placed against the myocardium and the catheter located within the inner guiding introducer is withdrawn, a vacuum may be created within the inner guiding introducer if no vents are provided. If such vacuum is formed, air may be forced back into the guiding introducer by the reintroduction of a catheter into the lumen of the guiding introducers. Such air embolism could cause problems to the patient including the possibility of a stroke, heart attack or other such problems common with air embolisms in the heart. The addition of vents near the distal tip of the guiding introducers prevents the formation of such vacuum by permitting fluid, presumably blood, to be drawn into the lumen of the guiding introducers as the catheter is being removed, thus preventing the possibility of formation of an air embolism.

Variances in size or shape of the pair of guiding introducers are also intended to encompass pediatric uses, although the preferred use is for adult human hearts. It is well recognized that pediatric uses may require reductions in size of the various sections of the guiding introducers in particular the first section, but without any significant modification to the shape or curves of the guiding introducers. However, because incremental changes can be made in the overall shape of the pair of guiding introducers, the system can better adjust to differing shapes and sizes of heart than can a single guiding introducer.

Figure 1A:
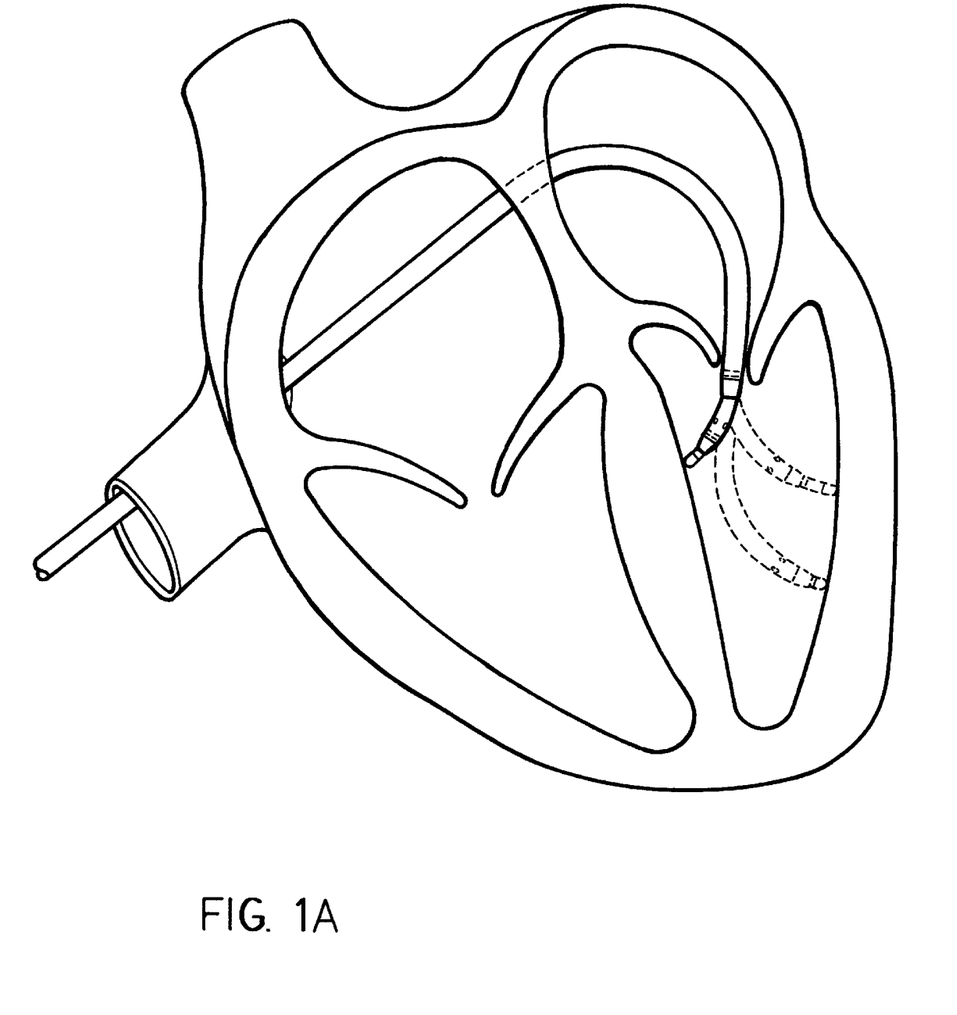
FIG. 1A is a cross-section of the left side of the heart showing the placement of the guiding introducer system in the left ventricle with the distal end of an ablation catheter extending from the distal end of the outer guiding introducer to ablate in three different locations along the walls of the left ventricle.
Figure 1B:
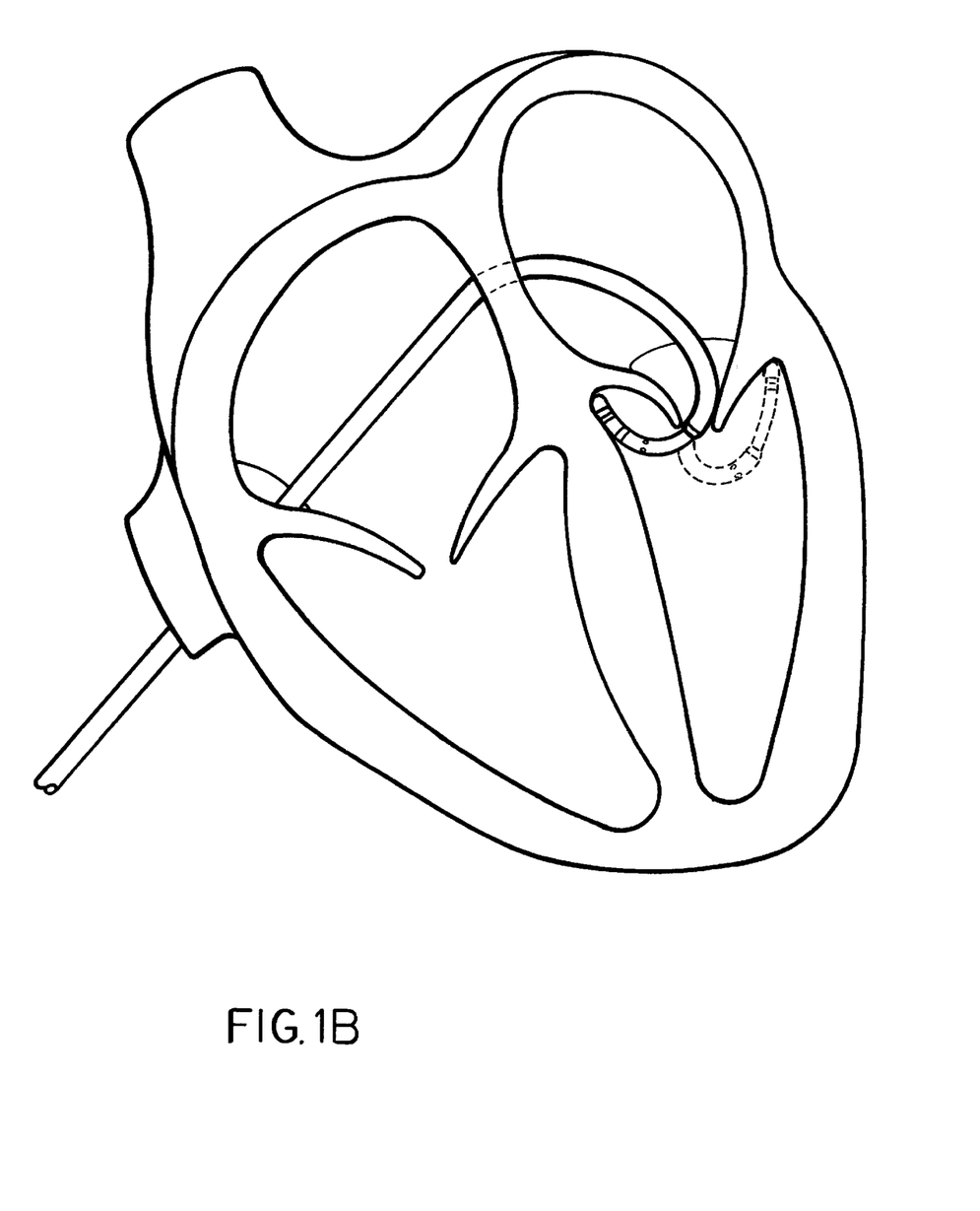
FIG. 1B is a cross-section of the left side of the heart showing the placement of the guiding introducer system in the left ventricle with the distal end of an ablation catheter extending from the distal end of the outer guiding introducer to ablate in two different locations under the mitral valve.
Figure 2A:
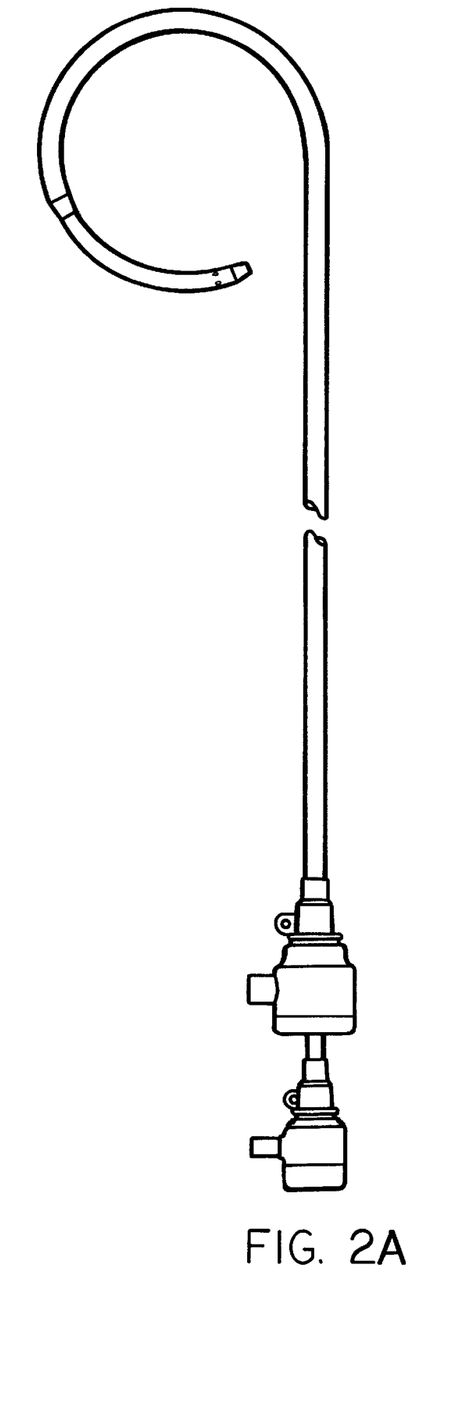
FIG. 2A is a side view of the inner and outer guiding introducers in combination with the distal end of the inner guiding introducer extended from the distal end of the outer guiding introducer.
Figure 2B:
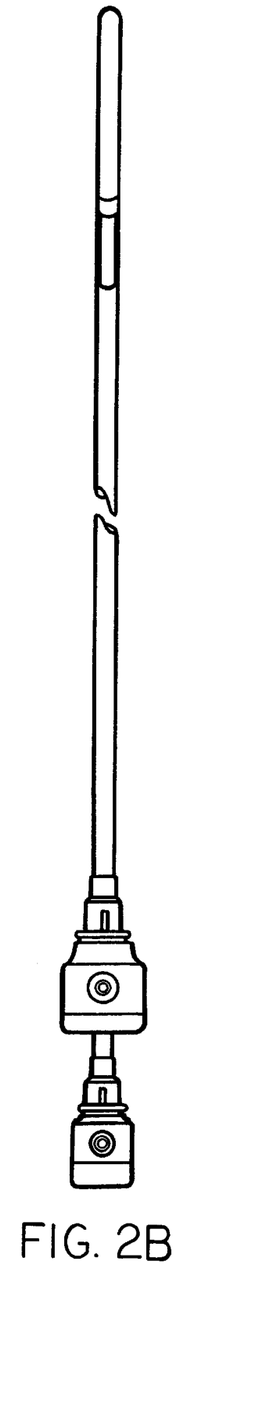
FIG. 2B is a side view of the inner and outer guiding introducers in combination as shown in FIG. 2A rotated 90 degrees from the position shown in FIG. 2A when viewed from the perspective of the proximal end of the inner and outer guiding introducers.
Figure 3A:
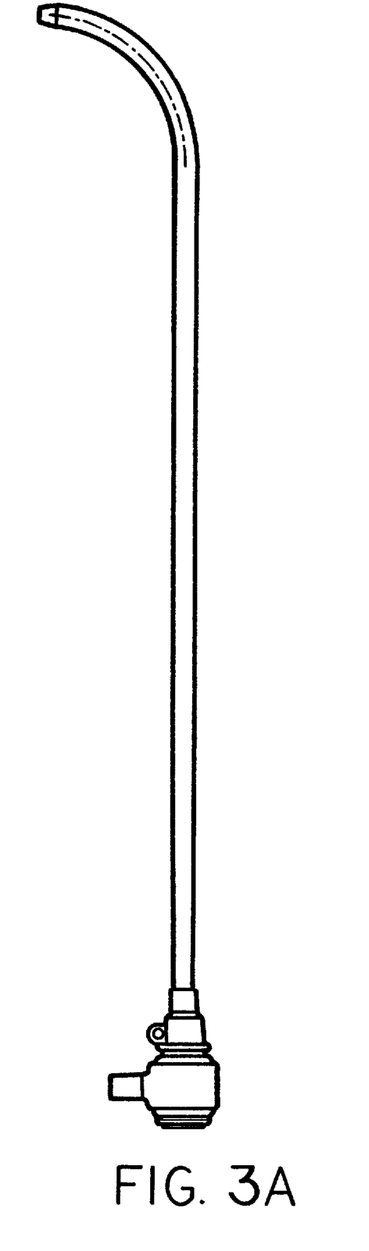
FIG. 3A is a side view of the inner guiding introducer attached to a hemostasis valve and side port with the side port directed to the left of the inner guiding introducer.
Figure 3B:
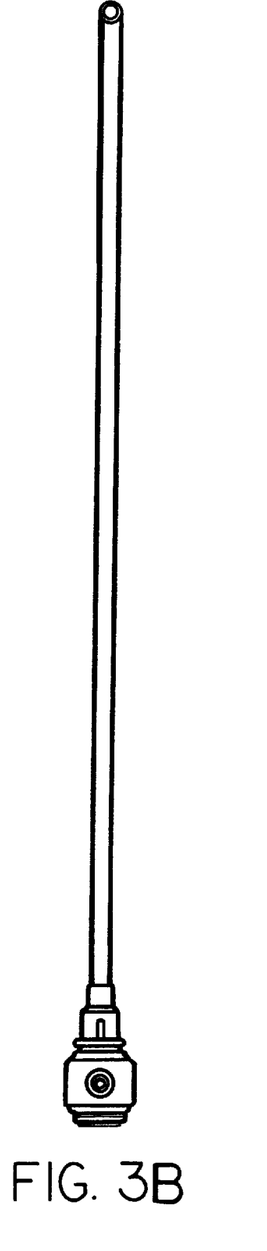
FIG. 3B is a side view of the inner guiding introducer of FIG. 3A rotated 90 degrees clockwise from the position shown in FIG. 3A when viewed from the perspective of the proximal end of the inner guiding introducer.
Figure 4A:
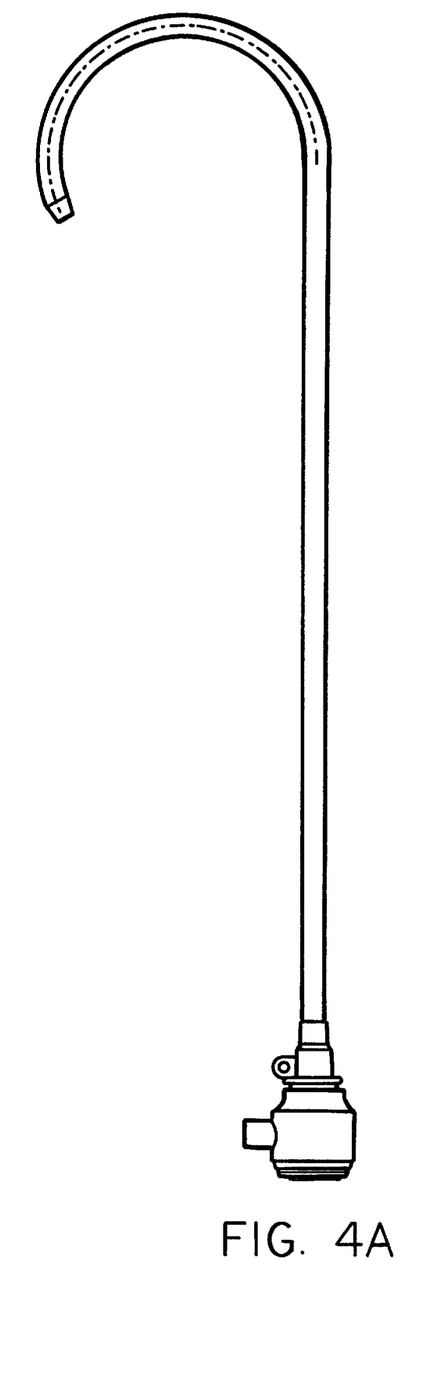
FIG. 4A is a side view of the outer guiding introducer attached to a hemostasis valve and side port with the side port directed to the left of the outer guiding introducer.
Figure 4B:
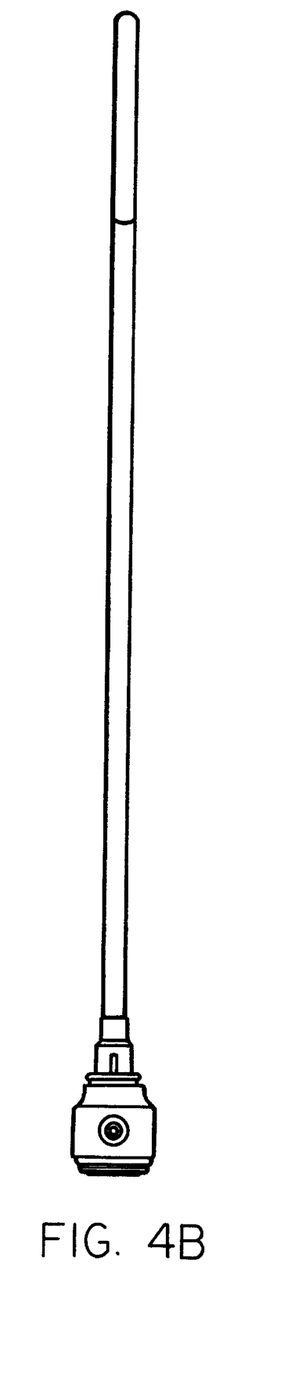
FIG. 4B is a side view of the outer guiding introducer of FIG. 4A rotated 90 degrees clockwise from the position shown in FIG. 4A when viewed from the perspective of the proximal end of the outer guiding introducer.

In operation, a modified Seldinger technique is normally used for the insertion of a catheter into either an artery or vein of the body. Using this procedure, a small skin incision is made at the appropriate location to facilitate the catheter and dilator passage. A soft flexible tip of an appropriate sized guidewire is inserted through and a short distance beyond a needle which has been introduced into the vessel. Firmly holding the guidewire in place, the needle is removed. The guidewire is then advanced through the vessel into the right atrium. With the guidewire in place, a dilator is then placed over the guidewire with the pair of guiding introducers placed over the dilator. The dilator and pair of guiding introducers generally form an assembly to be advanced together along the guidewire into the right atrium. After insertion of the assembly, the guidewire is then withdrawn. A Brockenbrough or trocar needle is then inserted through the lumen of the dilator to the right atrium to be used to create an opening through the interatrial septum, preferably at the fossa ovalis. The tip rests against the interatrial septum at the level of the fossa ovalis. The Brockenbrough needle is then advanced within the dilator to the fossa ovalis. After the opening is made through the interatrial septum, the needle, dilator and pair of guiding introducers are advanced into the left atrium. After the pair of guiding introducers are advanced through the interatrial septum into the left atrium, the Brockenbrough or trocar and dilator are removed, leaving the pair of guiding introducers in the left atrium. The distal tips of the inner and outer guiding introducers are then advanced through the mitral valve into the left ventricle. The catheter to be used for analysis and/or treatment of the ventricular tachycardia or other arrhythmia associated with the left ventricle, such as WPW, about the mitral valve is then advanced through the lumen of the pair of guiding introducers and is placed at an appropriate location in the left ventricle. See FIG. 1. By extending and withdrawing the inner guiding introducer from the outer guiding introducer and by rotating the inner guiding introducer within the outer guiding introducer, great variances in the overall shape of the guiding introducer system can be achieved.

By movement of the inner guiding introducer within the outer guiding introducer in conjunction with fluoroscopic viewing, the distal portion of the inner guiding introducer can be manipulated to direct the distal end of a catheter to a specific internal surface within the left ventricle. See FIGS. 1A and 1B. In addition, by providing sufficient rigidity, the distal end of the inner guiding catheter can be maintained in that fixed location or surface position of the endocardial structure to permit it to act as a stationary platform for the appropriate procedures to be performed. If sensing procedures are involved, the pair of guiding introducers are placed in the desired location. At that point, the electrical activity of the heart peculiar to that location can be precisely determined by use of an electrophysiology catheter placed within the guiding introducers and extended from the distal tip of the inner guiding introducer to the surface of the heart. As the pair of guiding introducers permit precise location of catheters, an ablation catheter may be placed at the precise location necessary for destruction of the cardiac tissue by the use of energy, for example, radio frequency, thermal, laser or direct current (high energy direct, low energy direct and fulgutronization procedures). The precise placement of the ablation catheter tip on the cardiac tissue is important as there will be no dilution of the energy delivered due to unfocused energy being dissipated over the entire cardiac chamber and lost in the circulating blood by constant movement of the tip of the ablating catheter. This permits a significantly reduced amount of energy to be applied, while still achieving efficient ablation. Further, time used to perform the procedure is significantly reduced over procedures where no guiding introducers are used.

It will be apparent from the foregoing that while particular forms of the invention have been illustrated and described, various modifications can be made without departing from the spirit and scope of the invention. Accordingly, it is not intended that this invention be limited except as by the appended claims.

We claim:

1. A guiding introducer system for treatment of arrhythmia associated with the left ventricle from the ventricular side comprising a precurved inner guiding introducer and a precurved outer guiding introducer, wherein the outer guiding introducer is formed in a predetermined shape designed to extend through an interatrial septum to a mitral valve of a human heart, wherein said guiding introducers are used in combination.

2. The guiding introducer system of claim 1 wherein a dilator containing distal and proximal ends is used in conjunction with the inner and outer guiding introducers, wherein said dilator curves at its distal end in a curve with an arc of about 20 to about 70 degrees.

3. The guiding introducer system of claim 1 wherein the inner guiding introducer comprises a first and second sections each with proximal and distal ends, wherein the first section is a generally elongated straight section, wherein merged with the distal end of said first section is the second section which contains a curved section with a radius of about 0.5 to about 1.5 in. to form an arc of approximately 45 to 135 degrees ending in the distal end of the second section of the inner guiding introducer.

4. The guiding introducer system of claim 3 wherein a plurality of vents is provided near the distal end of the second section of the inner guiding introducer.

5. The guiding introducer system of claim 3 wherein tip markers are secured to the inner guiding introducer.

6. The guiding introducer system of claim 1 wherein the outer guiding introducer comprises a first and second sections each with proximal and distal ends, wherein the first section is a generally elongated straight section, wherein merged with the distal end of said first section is the second section which contains a curved portion, curving in a radius of about 0.5 to about 1.5 in. to form an arc of about 145 to about 260 degrees, ending in the distal end of the second section of the outer guiding introducer.

7. The guiding introducer system of claim 6, wherein a plurality of vents is provided near the distal end of the second section of the outer guiding introducer.

8. The guiding introducer system of claim 6 wherein tip makers are secured to the outer guiding introducer.

9. The guiding introducer system of claim 1 wherein the outer guiding introducer comprises a first and second section each with proximal and distal ends, wherein the first section is a generally elongated straight section, wherein merged with the distal end of the first section is the second section, wherein the second section contains a compound curved section containing a first curved portion and a second curved portion, wherein the first curved portion has a radius of about 0.5 to about 1.5 inches and an arc of about 10 to about 50 degrees and the second curved portion has a radius of about 0.5 to about 1.5 inches and an arc of about 135 to about 225 degrees.

* * * * *